United States Patent
Bloemer et al.

(10) Patent No.: US 6,645,361 B1
(45) Date of Patent: Nov. 11, 2003

(54) ELECTROCHEMICAL GAS SENSOR

(75) Inventors: Bernhard Bloemer, Stuttgart (DE); Rainer Strohmaier, Stuttgart (DE); Carsten Springhorn, Stuttgart (DE); Detlef Heimann, Gerlingen (DE); Hans-Joerg Renz, Leinfelden-Echterdingen (DE); Harald Neumann, Farmington Hills, MI (US); Margret Schuele, Weil der Stadt (DE); Bernd Schumann, Rutesheim (DE); Thomas Moser, Schwieberdingen (DE); Sabine Thiemann-Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/936,815
(22) PCT Filed: Mar. 11, 2000
(86) PCT No.: PCT/DE00/00769
§ 371 (c)(1),
(2), (4) Date: Jan. 14, 2002
(87) PCT Pub. No.: WO00/57169
PCT Pub. Date: Sep. 28, 2000

(30) Foreign Application Priority Data
Mar. 18, 1999 (DE) .......................................... 199 12 102

(51) Int. Cl.$^7$ ............................................. G01N 27/407
(52) U.S. Cl. ........................ 204/426; 204/425; 204/427; 205/781

(58) Field of Search .................................. 204/421–429

(56) References Cited

U.S. PATENT DOCUMENTS

| | | | |
|---|---|---|---|
| 5,098,549 A | * | 3/1992 | Friese et al. |
| 5,902,469 A | * | 5/1999 | Kato et al. |
| 6,214,207 B1 | * | 4/2001 | Miyata et al. |
| 6,332,965 B1 | * | 12/2001 | Sugiyama et al. |

FOREIGN PATENT DOCUMENTS

| | | |
|---|---|---|
| DE | 198 27 469 | 1/1999 |
| EP | 0 678 740 | 10/1995 |
| EP | 0 869 356 | 10/1998 |
| EP | 0 897 112 | 2/1999 |

* cited by examiner

Primary Examiner—T. Tung
(74) Attorney, Agent, or Firm—Kenyon & Kenyon

(57) ABSTRACT

An electrochemical gas sensor for determining the concentration of gas components in a gas mixture, in particular for determining NOx and HC. The gas sensor includes a first measuring gas space which is connected to the measuring gas, and a second measuring gas space which is connected to the first measuring gas space by a connecting channel. Furthermore, a first electrode and a second electrode, arranged in the first measuring gas space, and at least one third electrode arranged in the second measuring gas space, and at least one fourth electrode are provided. The two measuring gas spaces are arranged in layer planes on top of one another and are separated from one another by at least one oxygen ion conducting layer, the connecting channel passing through the oxygen ion conducting layer.

22 Claims, 2 Drawing Sheets

ELECTROCHEMICAL GAS SENSOR

The present invention relates to an electrochemical gas sensor for determining the concentration of gas components in gas mixtures, in particular for determining the concentration of NOx and HC according to the preamble of independent claims 1 and 13.

BACKGROUND INFORMATION

European Patent Application 678 740 A1 describes a gas sensor of the aforementioned type for determining the NOx concentration in a gas mixture, in which two measuring gas spaces, each containing a pump cell, are arranged next to one another in a layer plane of a planar, oxygen ion conducting ceramic substrate. The measuring gas flows through a first diffusion opening into the first measuring gas space in which a first internal pump electrode is arranged. An external pump electrode is directly exposed to the measuring gas. The first internal pump electrode and the external pump electrode form the first pump cell. A predetermined oxygen partial pressure is set in the first measuring gas space via the first pump cell by pumping oxygen in and out. A concentration cell (Nernst cell) has a measuring electrode and a reference electrode connected to the atmosphere; the measuring electrode is arranged in the first measuring gas space. In order to set a constant oxygen partial pressure in the first measuring gas space, the voltage (electromotive force) of the concentration cell is controlled at a constant value via a pump voltage of the first pump cell. The first and second measuring gas spaces are connected by a connecting channel, which represents another diffusion opening; the atmosphere set at a constant oxygen partial pressure diffuses into the second measuring gas space via the connecting channel. Another internal pump electrode, which works together with the reference electrode arranged in the atmosphere reference channel and forms the second pump cell, is arranged in the second measuring gas space. The second internal pump electrode is made of a material, for example, rhodium, which reduces NO to $N_2$ and $O_2$. The reduced oxygen occurring at the second internal pump electrode is pumped, via a voltage applied to the pump, to the reference electrode and there it is released into the atmosphere. Since the atmosphere in the first measuring gas space is held at a constant oxygen partial pressure, the pump current for removing the reduced oxygen from the second measuring gas space is proportional to the NOx concentration. The measuring gas spaces and pump cells arranged in series are kept at different temperatures, the temperature at the electrodes in the first measuring gas space being set lower than the temperature at the electrode in the second measuring gas space. The sensor element design is relatively complicated and is only suitable for determining NOx.

ADVANTAGES OF THE INVENTION

The gas sensor according to the present invention having the characterizing features of claim 1 has the advantage that a basic sensor routinely manufactured for determining the lambda value of gas mixtures is used, to which only at least one further solid electrolyte layer having two additional electrodes has to be added. A sensor known as broad-band sensor, having a pump cell containing an internal and external pump electrode and a concentration cell containing a measuring electrode and a reference electrode, is used as the basic sensor. The measuring electrode and the internal pump electrode are arranged in a gas space opposite one another. In the sensor element according to the present invention this gas space forms the second measuring gas space. The use of a routinely manufactured basic lambda sensor offers considerable cost advantages compared to a sensor element design that is specialized for each application.

Another aspect of the present invention is, according to the characterizing features of claim 8, that the gas sensor can be used both as an NOx sensor and as an HC sensor with a single sensor element design. Only the taps at the electrode terminals are to be selected and the analysis circuit is to be adapted accordingly for either application. When the gas sensor is used as an HC sensor, the first electrode arranged in the first measuring gas space is used as a mixed potential electrode. When the gas sensor is used as an NOx sensor, the third electrode arranged in the second measuring gas space is used as an NOx reducing electrode. Additional cost advantages result through the wide application of the gas sensor.

The measures described in the subclaims allow advantageous refinements of and improvements on the sensor element presented in the main claim. The arrangement of two gas inlet openings symmetric with respect to the connecting channel ensures sufficient gas exchange of the measuring gas with the first measuring chamber and thus a short response time. In addition, this allows higher pump currents for the first pump cell.

BRIEF DESCRIPTION OF THE DRAWINGS

One embodiment of the present invention is illustrated in the drawing and described in detail in the description that follows.

DETAILED DESCRIPTION OF THE EMBODIMENT

Figure 1:
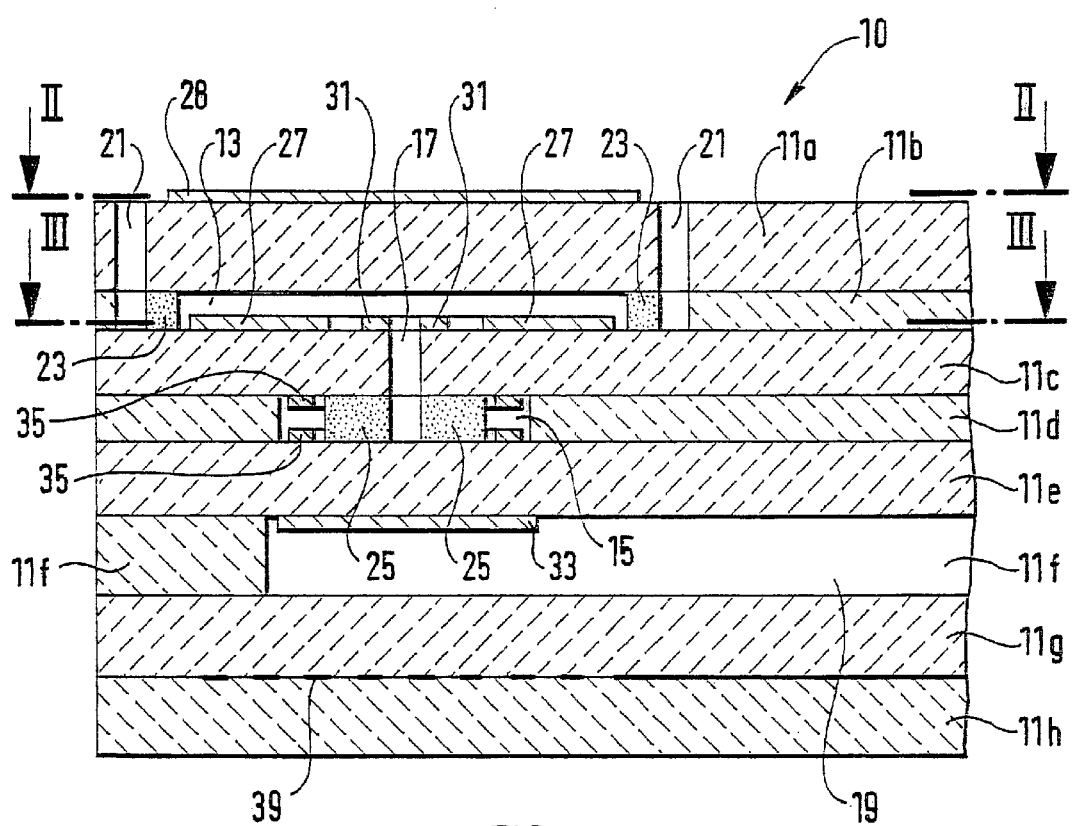
FIG. 1 shows a cross-section through a sensor element of a gas sensor according to the present invention.
Figure 2:
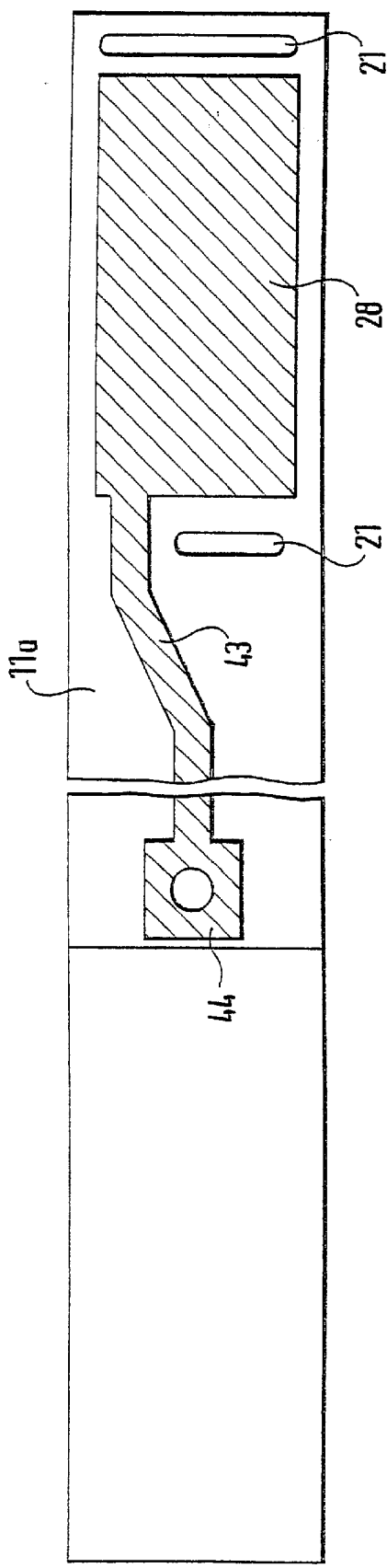
FIG. 2 shows a section through a layer plane according to line II—II in FIG. 1.
Figure 3:
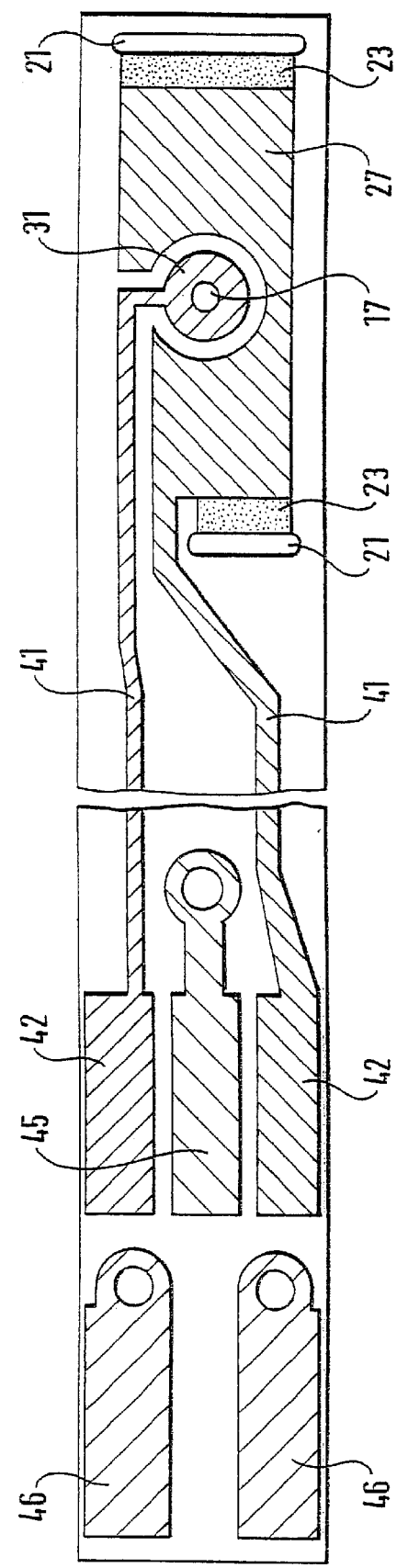
FIG. 3 shows a section through a layer plane according to line III—III in FIG. 1.

FIGS. 1, 2, and 3 show a schematic design of a preferred embodiment of the present invention. A planar sensor element 10 of an electrochemical gas sensor has, for example, a plurality of oxygen ion conducting solid electrolyte layers 11a, 11b, 11c, 11d, 11e, 11f, 11g, and 11h. Solid electrolyte layers 11a to 11h are designed as ceramic foils and form a planar ceramic body. The integrated form of the planar ceramic body of sensor element 10 is produced by laminating together the ceramic foils imprinted with function layers and subsequent sintering of the laminated structure in a way that is known per se. Each solid electrolyte layer 11a to 11h is made of oxygen ion conducting solid electrode material such as stabilized $ZrO_2$, for example.

Sensor element 10 has a first measuring gas space 13 and a second measuring gas space 15. The two measuring gas spaces 13, 15 are located on top of one another in different layer planes and are connected to one another by a connecting channel 17, designed as a bore hole, for example. Independently of the two measuring gas spaces 13, 15, a reference gas channel 19, whose one end leads out of the planar body of sensor element 10 and is connected to the atmosphere, is arranged, for example, in an additional layer plane.

Sensor element 10 also has two gas inlet openings 21, which conduct the measuring gas into first measuring gas space 13. The two gas inlet openings 21 are arranged symmetrically with respect to a plane passing through the center line of connecting channel 17, for example (FIG. 3). A first diffusion barrier 23 made of porous ceramic material, for example, is formed at the inlets to first measuring gas space 13 in the direction of diffusion of the measuring gas downstream from gas inlet openings 21. It is also conceivable that gas inlet openings 21 themselves be filled with a porous ceramic material, so that diffusion barrier 23 is then located within gas inlet openings 21.

A second diffusion barrier 25 is formed in the direction of diffusion of the measuring gas at the end of connecting channel 17 and upstream from second measuring gas space 15. Second measuring gas space 15 has a circular design, for example, so that second diffusion barrier 25 is also positioned annularly around the opening, located at the flow direction end of connecting channel 17.

A first internal electrode 27 and a second internal electrode 31 are arranged in first measuring gas space 13. An external electrode 28, which may be covered by a porous protective layer (not shown) and is directly exposed to the measuring gas, is located on the external large surface of solid electrolyte layer 11a. In the present embodiment, internal electrodes 27, 31 are arranged in series in the direction of diffusion of the measuring gas. It is, however, also possible to arrange internal electrodes 27, 31 opposite one another in the first measuring gas space.

A third internal electrode 35, which has two annular partial electrodes opposite one another in the present embodiment, is located in second measuring gas space 15. An additional electrode 33, exposed to atmospheric air, is located in reference channel 19. However, an embodiment in which fourth electrode 33 is also exposed to the measuring gas is also conceivable.

In order to use sensor element 10 both as an NOx sensor and an HC sensor, first internal electrode 27 and third internal electrode 35 must be made of special electrode materials.

For the mode of operation as an HC sensor, first internal electrode 27 is made of a material that lets this electrode operate as a mixed potential electrode, the mixed potential electrode not being capable or not being fully capable of catalyzing the establishment of gas equilibrium of the gas mixture. Gold or a gold/platinum alloy preferably having 1 wt. % gold is such a material, for example. External electrode 28, second internal electrode 31, and additional electrode 33 are made of a catalytically active material, for example, platinum.

For the mode of operation as an NOx sensor, third internal electrode 35 arranged in second measuring gas space 15 is made of a material capable of catalytically reducing NOx. Rhodium or a rhodium/platinum alloy is such a material, for example. It is important for operation as an NOx sensor that electrodes 27, 31, upstream from NOx-sensitive electrode 35 in the direction of diffusion of the measuring gas allow essentially no reduction of NOx. The electrode material for all electrodes is used in the known manner as cermet to be sintered with the ceramic foils.

According to FIGS. 2 and 3, contact points 42 of electrodes 27 and 31, formed on the surface of sensor element 10, are connected to printed conductors 41 running in the layer plane between solid electrolyte layers 11b and 11c. Contact point 44 of external electrode 28, leading to the layer plane underneath it and forming another contact point 45 there, is connected to a printed conductor 43 on the large surface of solid electrolyte layer 11a. The two partial electrodes opposite one another of electrode 35 are contacted within the ceramic substrate and with additional printed conductors (not shown) run to additional contact points 46 formed on the surface of sensor element 10 like additional electrode 33.

An electric resistance heater 39 is furthermore embedded in the ceramic body of sensor element 10 between two electrical insulation layers not shown in detail. Resistance heater 39 is used for heating sensor element 10 to the required operating temperature. Electrodes 27, 28, 31, 33, 35 arranged essentially on top of one another are exposed to essentially the same temperature. No attempt is made to set specific temperature differences at the individual electrodes, which would not be possible. Resistance heater 39 has heater contact points (not shown) on the external large surface of sensor element 10 opposite contact points 42, 45, 46.

The structure of sensor element 10 according to the present invention as shown in FIG. 1 uses a broad-band sensor for determining the lambda value as a basic sensor. The basic sensor is formed by solid electrolyte layers 11c, 11d, 11e, 11f, 11g, and 11h and by electrodes 27, 33, and 35. Electrodes 27 and the first partial electrode of electrode 35, opposite electrodes 27 in measuring gas space 15 form a pump cell in the broad-band sensor, and the second partial electrode of electrode 35, together with additional electrode 33, forms the concentration cell, electrode 33 acting as a reference electrode. As a refinement of sensor element 10 according to the present invention, electrodes 27 and 28 of solid electrode layers 11a and 11b are connected to the basic sensor, measuring gas space 13 being located in solid electrolyte foil 11b. However, an embodiment in which only solid electrolyte foil 11a is used is also conceivable. In this embodiment, measuring gas space 13 is then also integrated in solid electrolyte foil 11a.

The above-described sensor element 10 can be used both as an NOx sensor and as an HC sensor, individual electrodes 27, 28, 31, 33, 35 performing different functions depending on the application. For this purpose, electrodes 27, 28, 31, 33, 35 are electrically interconnected according to the functions of the electrodes.

Operation as an NOx Sensor

When sensor element 10 is used as an NOx sensor, external electrode 28 and first internal electrode 27 are operated as pump electrodes of a first pump cell. Second internal electrode 31 is wired with additional electrode 33 acting as a reference electrode as a concentration cell. A pump voltage is applied to electrodes 27, 28, through which a constant oxygen partial pressure is set in first measuring gas space 13 by pumping oxygen in or out. The pump voltage applied to electrodes 27, 28 is controlled so that a constant voltage value, for example, 450 mV, is set at electrodes 31, 33 of the concentration cell. This voltage corresponds to a lambda value=1. For a lean measuring gas (lambda>1), oxygen is pumped by the first pump cell out of first measuring gas space 13. For a rich measuring gas (lambda<1), oxygen is pumped into first measuring gas space 13 from the measuring gas. By selecting the electrode material and/or by applying an appropriate pump voltage, it is guaranteed that no NOx is pumped away at electrodes 27, 31 when pumping oxygen.

The measuring atmosphere adjusted to a constant oxygen partial pressure is now pumped via connecting channel 17 and second diffusion barrier 25 to second measuring gas space 15. Third internal electrode 35 located in second measuring gas space 15 is operated, together with additional electrode 33, as a second pump cell. Because of the catalytic material, third internal electrode 35 acts as an NOx-sensitive electrode, at which the NOx is reduced according to the reaction NO→½N$_2$+½O$_2$. Reference electrode 33, working together with electrode 31 operates simultaneously as a second pump electrode, at which the oxygen pumped away from second measuring gas space 15 is released to the atmosphere. Due to diffusion barrier 25 forming a diffusion resistance, the NOx diffusing into second measuring gas space 15 is fully pumped away from electrode 35. Thus a limit current is established at the electrochemical cell acting as an additional pump cell, providing the NOx concentration when picked up as a measuring signal.

Operation as an HC Sensor

If sensor element 10 is used as an HC sensor, electrodes 27, 28, 31, 33, 35 are interconnected in a manner that is different from that used for the NOx sensor application. Electrodes 33, 35 are operated as pump electrodes but, contrary to the NOx application, so that oxygen is pumped from the atmosphere into second measuring gas space 15. In doing so, an artificial measuring atmosphere with a higher oxygen concentration (lambda>1) compared to the measuring gas is created in second measuring gas space 15, the measuring atmosphere being pumped back into first measuring gas space 13 via the connecting channel. First diffusion barrier 23 prevents oxygen from escaping unhindered into the measuring gas, a higher oxygen partial pressure being maintained in first measuring gas space 13.

It is important for the mode of operation as an HC sensor that first internal electrode 27 be a "poisoned" catalytically active electrode, which does not establish or at least does not fully establish equilibrium of the gas mixture as a mixed potential electrode. Operation as an HC sensor also makes use of the fact that a measuring signal at the electrochemical sensors, representing the HC concentration, differs from the oxygen concentration signal curve in a characteristic manner in lean measuring gas (lambda>1) only.

Due to the fact that the higher oxygen concentration in first measuring gas space 13 differs from that in reference channel 19 a first voltage is established between electrode 27 acting as a mixed potential electrode and electrode 33, which correlates with the HC concentration and the oxygen concentration difference. A second voltage signal between catalytically active electrode 31 and electrode 33 corresponds to the oxygen concentration in measuring gas space 13. The difference between the two voltages corresponds to the HC concentration in the measuring gas. This voltage difference is also applied between electrode 27 and electrode 31, so that the voltage picked up between electrodes 27, 31 provides the HC concentration as a measuring signal. It is, however, also possible to pick up the current driven by the voltage between electrodes 27, 31 as the measuring signal.

Electrode 28 has no function in the case of an HC sensor and is therefore not taken into consideration in the wiring of sensor element 10.

In another embodiment of the present invention a special sensor element is used for each application as an NOx sensor and an HC sensor. In this case, preferably the same layer structure of the solid electrolyte layers is used for both the NOx sensor and the HC sensor. There are differences in the material for electrode 27 and electrode 35. In an NOx sensor, electrode 31 cannot be manufactured from a mixed potential material, but may be made of the same material as electrode 27. In the case of an HC sensor, the material of electrode 35 may not be NOx reducing, but can be made of the same material as electrode 31 or even electrode 27. Since the electrodes are applied to the ceramic foils using thick layer technology, such an embodiment still offers cost advantages, since the number of foils and the expensive lamination method remain identical.

In addition, the sensor is suitable for determining ammonia in gas mixtures. For this purpose, platinum is embedded in first diffusion barrier 23 which oxidizes ammonia to NOx due to its catalytic effect.

What is claimed is:

1. An electrochemical gas sensor for determining concentration of gas components in a gas mixture comprising:
    a first measuring gas space in contact with a measuring gas, the first measuring gas space including a first electrode and a second electrode;
    a second measuring gas space including at least one third electrode, the at least one third electrode including two partial electrodes arranged opposite one another in the second measuring gas space;
    a connecting channel connecting the first measuring gas space to the second measuring gas space;
    at least one oxygen ion conducting layer separating the first measuring gas space from the second measuring gas space; and
    at least one fourth electrode;
    wherein the first and second measuring gas spaces are arranged in layer planes on top of one another.

2. The gas sensor of claim 1, further comprising:
    at least two gas inlet openings leading into the first measuring gas space, the at least two gas inlet openings being arranged symmetrically with respect to a plane passing through a center line of the connecting channel.

3. The gas sensor of claim 1, wherein the at least one third electrode includes a material capable of reducing a No$_x$ gas component.

4. The gas sensor of claim 3, wherein the at least one third electrode includes one of rhodium and a rhodium/platinum alloy.

5. The gas sensor of claim 1, wherein the first and second electrodes are arranged in series in the first measuring gas space in a direction of diffusion of the measuring gas.

6. The gas sensor of claim 1, wherein the first electrode includes a material that does not fully catalyze an establishment of equilibrium of the gas mixture.

7. The gas sensor of claim 1, wherein the first electrode includes one of gold and a platinum/gold alloy.

8. The gas sensor of claim 1, further comprising:
    an additional electrode exposed to the measuring gas, a pump voltage being applied between the additional electrode and the first electrode to establish a constant oxygen partial pressure in the first measuring gas space;
    wherein the at least one third electrode and the at least one fourth electrode form an additional pump cell, the pump cell generating a pump current picked up as a measuring signal.

9. The gas sensor of claim 1, wherein the second electrode and the at least one fourth electrode form a concentration cell, the concentration cell being controlled at a constant voltage.

10. The gas sensor of claim 1, wherein the at least one third electrode and the at least one fourth electrode are coupled and form pump cells for pumping oxygen into the second measuring gas space, the first electrode being designed as a mixed potential electrode and forming a concentration cell with the at least one fourth electrode, the voltage of the concentration cell being picked up as a measuring signal.

11. The gas sensor of claim 1, wherein:
    the two partial electrodes are not in direct physical contact with each other.

12. The gas sensor of claim 1, wherein:

the connecting channel includes a bore.

13. The gas sensor of claim 1, wherein:

the two partial electrodes include a first partial electrode and a second partial electrode, the first partial electrode performs a first function, and the second partial electrode performs a second function.

14. An electrochemical gas sensor for determining concentration of gas components in a gas mixture, comprising:

a first measuring gas space in contact with a measuring gas, the first measuring gas space including a first electrode and a second electrode, the first electrode including a material that does not fully catalyze an establishment of equilibrium in the gas mixture;

a second measuring gas space including at least one third electrode, the at least one third electrode including a material capable of reducing $NO_x$ gas components, the at least one third electrode including two partial electrodes arranged opposite one another in the second measuring gas space;

a connecting channel connecting the first measuring gas space to the second measuring gas space; and at least one fourth electrode.

15. The gas sensor of claim 14, wherein the first electrode includes one of gold and a platinum/gold alloy.

16. The gas sensor of claim 15, wherein the platinum/gold alloy includes 0.5 to 3 wt. % of gold.

17. The gas sensor of claim 16, wherein the platinum/gold alloy includes approximately 1 wt. % of gold.

18. The gas sensor of claim 14, wherein the at least one third electrode includes one of rhodium and a rhodium/platinum alloy.

19. The gas sensor of claim 14, further comprising:

at least one oxygen ion conducting layer separating the first measuring gas space from the second measuring gas space;

wherein the first and second measuring gas spaces are arranged in layer planes on top of one another and the connecting channel passes through the at least one oxygen ion conducting layer.

20. The gas sensor of claim 14, wherein:

the two partial electrodes are not in direct physical contact with each other.

21. The gas sensor of claim 14, wherein:

the connecting channel includes a bore.

22. The gas sensor of claim 14, wherein:

the two partial electrodes include a first partial electrode and a second partial electrode, the first partial electrode performs a first function, and the second partial electrode performs a second function.

* * * * *

UNITED STATES PATENT AND TRADEMARK OFFICE
CERTIFICATE OF CORRECTION

PATENT NO.   : 6,645,361 B1
DATED        : November 11, 2003
INVENTOR(S)  : Bernhard Bloemer et al.

It is certified that error appears in the above-identified patent and that said Letters Patent is hereby corrected as shown below:

Column 1,
Line 2, insert -- "FIELD OF THE INVENTION" --
Line 5, change "mixtures, in" to -- mixtures, and in --
Line 5, change "particular for" to -- particular relates to an electrochemical gas sensor for --
Line 11, change "Application" to -- Application No. --
Line 11, delete "Al"
Line 11, change "a gas" to -- a conventional gas --
Line 25, change "atmosphere; the" to -- atmosphere. The --
Line 31, change "opening; the" to -- opening, and the --
Line 32, change "set" to -- is set --
Line 32, change "diffuses" to -- which diffuses --
Line 52, change "The" to -- This --
Line 55, change "ADVANTAGES" to -- SUMMARY --
Line 56, delete "having the ...claim 1"
Line 61, change "has to be" to -- is --

Column 2,
Line 1, change "invention" to -- invention, --
Line 6, change "Another aspect of the" to -- The gas sensor according to the --
Lines 6-7, delete "is, according...the gas sensor"
Lines 9-10, change "Only the...and the" to -- The --
Line 11, change "application." to -- application by selection of taps at the electrode terminals. --
Lines 19-21, delete "The measures...main claim."
Lines 40-41, delete "OF THE EMBODIMENT"
Line 36, change ", and" to -- . --
Line 43, change "a preferred" to -- an --
Lines 52-53, delete "in a way...per se."
Line 62, change "whose one" to -- having an --
Line 62, change "leads" to -- leading --
Line 63, change "is" to -- being --

UNITED STATES PATENT AND TRADEMARK OFFICE
CERTIFICATE OF CORRECTION

PATENT NO. : 6,645,361 B1
DATED : November 11, 2003
INVENTOR(S) : Bernhard Bloemer et al.

It is certified that error appears in the above-identified patent and that said Letters Patent is hereby corrected as shown below:

Column 3,
Line 1, change "The" to -- According to one implementation, the --
Line 3, change "for example (FIG. 3)" to -- shown in FIG. 3 --
Line 4, change "23 made of" to -- 23 which may be --
Line 7, change "conceivable" to -- possible --
Line 14, change "second" to -- According to one implementation, a second --
Line 21, delete "is"
Line 32, change "an embodiment in which" to -- a --
Line 33, change "33" to -- 33 that --
Line 34, change "is also conceivable" to -- can also be included --
Line 38, change "must be made of special" to -- include certain --
Line 40, change "For the mode of operation as an HC sensor," to -- For operation in HC sensor mode, --
Line 41, change "is made of" to -- includes --
Line 41, change "lets this electrode" to -- enables this electrode to --
Lines 42-44, change "the mixed potential...of catalyzing" to -- which does not fully catalyze --
Line 45, change "Gold" to -- This material may be gold --
Line 45, delete "preferably"
Line 46, delete "is such a material"
Line 48, change "material, for example, platinum." to -- material, which may be platinum, for example. --
Line 50, change "the mode of operation as an $NO_X$ sensor," to -- operation in HC sensor mode, --
Line 54, change "It is important for operation as an $NO_X$ sensor that" to -- In $NO_X$ sensor mode --
Line 64, change "leading" to -- which leads --
Line 65, change "forming" to -- forms --

Column 4,
Line 6, delete "furthermore"
Line 11, delete "essentially"
Line 12, delete "essentially"
Lines 12-14, delete "No attempt...not be possible."
Line 27, change "As a refinement" to -- In an implementation --
Line 30, "change "sensor," to -- sensor, with --
Line 32, change "conceivable." to -- possible --

UNITED STATES PATENT AND TRADEMARK OFFICE
CERTIFICATE OF CORRECTION

PATENT NO. : 6,645,361 B1
DATED : November 11, 2003
INVENTOR(S) : Bernhard Bloemer et al.

It is certified that error appears in the above-identified patent and that said Letters Patent is hereby corrected as shown below:

Column 5,
Line 24, change "gas," to -- gas, allowing --
Line 25, change "being" to -- to be --
Line 26, change "It is important for" to -- In --
Line 26, change "sensor" to -- sensor, --
Line 27, change "that" to -- the --
Lines 27-28, delete "be a "poisoned"...electrode, which"
Line 53, change "invention" to -- invention, --
Line 59, change "cannot be" to -- is not necessarily --
Line 60, change "may not be" to -- is not --

Signed and Sealed this

Twenty-second Day of March, 2005

JON W. DUDAS
*Director of the United States Patent and Trademark Office*